(12) United States Patent
Hodges et al.

(10) Patent No.: US 10,921,274 B2
(45) Date of Patent: Feb. 16, 2021

(54) APPARATUS FOR IN VIVO DIELECTRIC SPECTROSCOPY

(71) Applicants: John W. Hodges, Ocoee, FL (US); Marc E. Rippen, SE Palm Bay, FL (US)

(72) Inventors: John W. Hodges, Ocoee, FL (US); Marc E. Rippen, SE Palm Bay, FL (US)

(*) Notice: Subject to any disclaimer, the term of this patent is extended or adjusted under 35 U.S.C. 154(b) by 0 days.

(21) Appl. No.: 16/734,534

(22) Filed: Jan. 6, 2020

(65) Prior Publication Data

US 2020/0217809 A1    Jul. 9, 2020

Related U.S. Application Data

(60) Provisional application No. 62/788,197, filed on Jan. 4, 2019.

(51) Int. Cl.
*G01N 27/02* (2006.01)
*G01N 27/22* (2006.01)
(Continued)

(52) U.S. Cl.
CPC ......... *G01N 27/026* (2013.01); *A61B 5/0538* (2013.01); *G01N 27/028* (2013.01); *G01N 27/221* (2013.01); *G01N 33/48707* (2013.01)

(58) Field of Classification Search
CPC .. G01N 27/026; G01N 27/221; G01N 27/028; G01N 33/48707; A61B 5/00;
(Continued)

(56) References Cited

U.S. PATENT DOCUMENTS

| 7,525,323 B1 | 4/2009 | Hopper et al. |
| 9,167,993 B2 | 10/2015 | Esenaliev et al. |

(Continued)

FOREIGN PATENT DOCUMENTS

| EA | 030390 | 7/2018 |
| EP | 2976008 | 4/2013 |

(Continued)

OTHER PUBLICATIONS

International Search Report and Written Opinion from the International Search Authority for International Application No. PCT/US/20/12356, dated Mar. 31, 2020, pp. 1-9.

*Primary Examiner* — Chu Chuan Liu
(74) *Attorney, Agent, or Firm* — The Concept Law Group, PA; Scott D. Smiley; Scott M. Garrett

(57) ABSTRACT

The apparatus includes a sensor having a multi-portion dielectric composite. A microstrip transmission line is formed on the dielectric composite and includes an input section, radiator portion, and an output section. The dielectric material adjacent the radiator portion is selected to substantially match that of the certain portions of a live organism being sensed, allowing other constituents of the organism to be sensed. This allow the radiator portion to effectively respond as if it were embedded inside the organism, removing substantial uncertainly from the measurement process. By then applying a plurality of signals to the sensor, the reflected and transmitted components of the signal can be measured and used to determine the amount of certain constituents are present in the organism.

20 Claims, 8 Drawing Sheets

(51) Int. Cl.
*G01N 33/487* (2006.01)
*A61B 5/0538* (2021.01)

(58) Field of Classification Search
CPC ....... A61B 5/05; A61B 5/0002; A61B 5/0507; A61B 5/14532; A61B 5/14546
See application file for complete search history.

(56) References Cited

U.S. PATENT DOCUMENTS

| | | |
|---|---|---|
| 9,833,178 B2 | 12/2017 | Aberg et al. |
| 10,188,325 B2 | 1/2019 | Esenaliev |
| 10,264,993 B2 | 4/2019 | Looney et al. |
| 2003/0072549 A1* | 4/2003 | Facer ................... G01N 22/00 385/129 |
| 2012/0150000 A1 | 6/2012 | Al-Shamma'a et al. |
| 2013/0190646 A1 | 7/2013 | Weinstein et al. |
| 2017/0164878 A1 | 6/2017 | Connor |
| 2017/0181658 A1 | 6/2017 | Dettmann et al. |
| 2018/0325431 A1 | 11/2018 | Guarin et al. |

FOREIGN PATENT DOCUMENTS

| | | |
|---|---|---|
| EP | 2458369 | 7/2014 |
| EP | 2440909 | 10/2016 |
| GB | 2428093 | 1/2007 |
| WO | 2009078814 | 6/2009 |
| WO | 2011100390 | 8/2011 |
| WO | 2012059741 | 5/2012 |
| WO | 2017013616 | 1/2017 |
| WO | 2018083379 | 5/2018 |
| WO | 2018092146 | 5/2018 |
| WO | 2019098947 | 5/2019 |

\* cited by examiner

APPARATUS FOR IN VIVO DIELECTRIC SPECTROSCOPY

CROSS-REFERENCE TO RELATED APPLICATION

This application claims priority to U.S. Provisional Patent Application No. 62/788,197 filed Jan. 4, 2019, the entirety of which is incorporated by reference.

FIELD OF THE DISCLOSURE

The present invention relates generally to sensors and related apparatuses for measuring biological properties of a living organism using an electric signal, and more particularly to using dielectric spectroscopy techniques to eliminate dielectric variability at the interface of a sensor and the living organism.

BACKGROUND OF THE DISCLOSURE

Variously known as swept frequency permittivity, resistive spectroscopy, impedance spectroscopy, or resistive pulse spectroscopy, the use of electromagnetic fields on the order of 1 Hz to tens of GHz to characterize the permittivity response of a biological sample over this broad range of frequencies, is more commonly referred to as dielectric spectroscopy. See H. Fricke, Philos. Mag. 14, 310 (1932), K. S. Cole and R. H. Cole, J. Chem. Phys. 9, 341 (1941), K. Asami, E. Gheorghiu, and T. Yonezawa, Biophys. J. 76, 3345 (1999), C. Prodan and E. Prodan, J. Phys. D 32, 335 (1999) and G. Smith, A. P. Duffy, J. Shen, and C. J. Olliff, J. Pharm. Sci. 84, 1029 (1995). The diverse terms used to describe such techniques reflect, in part, the fact that equivalent representations are possible for electrical properties. For example, representations of impedance as a complex number are equivalent to representations of conductance as a complex number, and also equivalent to representations of permittivity as a complex number. "Equivalent," in this sense, indicates that any of the above representations can be fully obtained from any other, via a straightforward mathematical transformation. Other such equivalent representations are also possible, and are included within the scope of this disclosure. Dielectric spectroscopy searches for permittivity fingerprints consisting of impedance or capacitance data in the frequency ranges of D.C. to RF and microwave propagation in the GHz range. See H. E. Ayliffe, A. B. Frazier, and R. D. Rabbitt, IEEE J. Microelectromech. Syst. 8, 50 (1999) and J. Hefti, A. Pan, and A. Kumar, Appl. Phys. Lett. 75, 1802 (1999). Ideally, different components in the solutions will have different dispersion patterns in different frequency ranges. For example, ideally the ions in the solutions show a particular dispersion characteristic, called alpha dispersion, in the frequency range of 1 Hz to >1 GHz. The macro species in the solutions such as cells or organelles-exhibit their own particular dispersion pattern, called beta dispersion, generally in the 1 kHz to 1 MHz range. Finally, in the frequency range extending from 1 MHz to hundreds of GHz, the solvents in the solution exhibit what is herein called gamma dispersion. See J. Gimsa and D. Wachner, Biophys. J. 75, 1107 (1998) and V. Raicu, Phys. Rev. E 60, 4677 (1999). In reality, the response of whole, living biological organism is not so clearly differentiated and there is considerable frequency overlap in the dispersion characteristics of the different components over the entire frequency range of interest. See H. P. Schwan and S. Takashima, Encyclopedia of Applied Physics (VCH, New York, 1993), Vol. 5, pp. 177-200, P. Debye, Polar Molecules (Dover, N.Y., 1929), G. De Gasperis, X. Wang, J. Yang, F. F. Becker, and P. R. C. Gascoyne, Meas. Sci. Technol. 9, 518 (1998), A. K. Jonscher, Nature (London) 267, 673 (1977). Access to a broad frequency range is important with biological samples, due to their chemical diversity. See B. Onaral, H. H. Sun, and H. P. Schwan, IEEE Trans. Biomed. Eng. 31, 827 (1984) and P. A. Cirkel, J. P. M. van der Ploeg, and G. J. M. Koper, Physica A 235, 269 (1997). RN Clarke (Ed.), "*A Guide to the Characterisation of Dielectric Materials at RF and Microwave Frequencies,*" Published by The Institute of Measurement & Control (UK) & NPL, 2003. J. Baker-Jarvis, M. D. Janezic, R. F. Riddle, R. T. Johnk, P. Kabos, C. Holloway, R. G. Geyer, C. A. Grosvenor, "*Measuring the Permittivity and Permeability of Lossy Materials: Solids, Liquids, Metals, Building Materials, and Negative-Index Materials,*" NIST Technical Note, 2005. "*Test methods for complex permittivity (Dielectric Constant) of solid electrical insulating materials at microwave frequencies and temperatures to 1650°,*" ASTM Standard D2520, American Society for Testing and Materials. Janezic M. and Baker-Jarvis J., "*Full-wave Analysis of a Split-Cylinder Resonator for Nondestructive Permittivity Measurements,*" IEEE Transactions on Microwave Theory and Techniques vol. 47, no. 10, October 1999, pg. 2014-2020. J. Krupka, A. P. Gregory, O. C. Rochard, R. N. Clarke, B. Riddle, J. Baker-Jarvis, "*Uncertainty of Complex Permittivity Measurement by Split-Post Dielectric Resonator Techniques,*" Journal of the European Ceramic Society No. 10, 2001, pg. 2673-2676. "*Basics of Measuring the Dielectric Properties of Materials*". Agilent application note. 5989-2589EN, Apr. 28, 2005. Accordingly, there has been extensive study and knowledge developed in the field of dielectric spectroscopy.

Dielectric spectra of living biological organisms reveal a rich variety of dynamic processes form the cellular level down to the analyte molecular level. Achieving a better characterization and understanding of these processes and compositions not only is of academic interest but also of high relevance for medical applications such as, for example, the determination of specific homeostasis processes of the human body and agricultural applications. These processes can be used, for example, in the detection of plant diseases which can greatly affect the total production of food and agricultural materials, and which could lead to high amount of losses in terms of quality, quantity and also in economic sense. Further, these processes can indicate chemical presence and levels for various compositions which are conventionally measured using intrusive means (e.g. drawing blood), and analyzing a sample taken from the organism or person.

The dielectric properties of biological cells can provide information regarding the cellular and molecular state of a given population of cells. These properties are mainly characterized by the beta-dispersion, a dielectric relaxation phenomenon, which is observed in the medium and high frequency (HF) to very high frequency (VHF) range of the radio spectrum. The beta-dispersion mechanism in many biological subjects is due to Maxwell-Wagner polarization (interfacial polarization) at the external and internal interfaces of the phospholipid membrane and is caused by the ability of biological cell membranes to impede electrical current. Additional contributions to the beta-dispersion in many biological subjects may be observed due to the presence of organelles, heterogeneity of the cell population, and other phenomena.

Many existing techniques for analyzing biological organisms, microorganisms, cells, or biological molecules outside their normal biological context done in vitro ("within the glass"), i.e., in a laboratory environment using test tubes, petri dishes, etc. These techniques undesirably change the characteristics of the organism being measured so that the organism is altered in undesirable ways, distorting the test results. They also require removal of bio-material from the organism.

Dielectric Spectroscopy techniques to estimate dielectric properties of biological cells In Vitro are discussed at, for example, U.S. Pat. Nos. 4,810,650, 4,965,206, 6,496,020, 6,596,507, and 7,930,110. In the known techniques to estimate biological property data, electrical property data are received by applying a signal to a solution of cells across multiple frequencies.

However, these techniques are limited to in vitro, or in glass measurements. Research has found that wide variation between in vitro and in vivo measurements can occur. Between beta- and gamma-relaxation, significant dispersion is observed, which, however, can be explained by a superposition of these relaxation processes and is not due to an additional delta-relaxation often found in biological matter.

Suitable measuring devices that can be used in performing dielectric spectroscopy are readily discernible to one of ordinary skill in the art. For example, there are three main forms of apparatus utilized to make Dielectric Spectroscopy measurements, these are the coaxial probe, free space methods, and transmission line methods. In some examples, measuring devices include a signal generator, receiver, and signal analyzer coupled to an apparatus for measuring electromagnetic properties of a sample. The resulting capacitance(s), or dielectric spectrum, will be affected by cell attributes such as morphology, membrane charge, organelles, health, and/or buildup or presence of metabolites within the cell, and the resulting capacitance(s) can therefore yield information about these attributes in real-time.

Resonant techniques for dielectric spectroscopy, while highly accurate, require the subject to be entirely placed into an electrically resonant chamber which are completely impractical for living organisms so are not considered here. Currently, in the field of dielectric spectroscopy the above methods for precision dielectric spectroscopy of biological tissue are typically not applied to the whole, living biological organism or greatly perturb the organism. These methods undesirably change the characteristics of the organism being measured so that the organism is altered in undesirable ways, distorting the test results.

The open-ended coaxial probe is a cut off section of transmission line. A material is typically measured by immersing the probe into a liquid or touching it to the flat face of a solid (or powder) material. The fields at the probe end "fringe" into the material and change as they come into contact with the material under test. The reflected signals in the form of S-parameters (S11) can be measured and related to the relative permittivity of the material as a function of frequency. The open-ended coaxial probe method is broadband and non-destructive. However, for biological in vivo measurements the method requires that the subject be a) semi-infinite in thickness, b) isotropic and homogeneous, c) a flat surface, and d) have no air gaps. The open-ended coaxial probe method is typically used in conjunction with a vector network analyzer (VNA) to record the frequency-dependent complex reflection coefficient. The permittivity over frequency of the sample is then calculated from the reflection coefficient at the probe aperture using standard inverse techniques.

Open-ended coaxial probes must be carefully calibrated so that the reflection-coefficient measurements are referenced to the probe aperture plane. This is usually done in one of two ways, which are: 1) using reference liquids for direct calibration at the open end of the probe or 2) using mechanical or electronic calibration standards at the connector plane combined with a model of the probe that translates the reference plane to the aperture. These requirement make using the open-ended coaxial probe highly impractical for use in measuring in vivo processes.

Free-space methods use antennas to focus radio energy at or through a sample of material without the need for a test fixture. This method is non-contacting and can be applied to materials to be tested under high temperatures and hostile environments. Like the open-ended coaxial probe method Free-space methods are broadband and non-destructive. However, for biological in vivo measurements the method is not practical because it requires large, flat, parallel-faced samples which is limited in biological subject by practical sample size to high frequencies in the microwave region.

Transmission line methods involve placing the material inside a portion of an enclosed transmission line. The line is usually a section of rectangular waveguide or coaxial airline. Both electrical permittivity $e_r^*$ and magnetic permeability $\mu_r^*$ are computed from the measurement of the reflected signal S-parameters (S11) and transmitted signal (S21). Like the open-ended coaxial probe method and free-space methods, transmission line methods are broadband. Unlike open-ended coaxial probe and free space methods, transmission line method are destructive because the biological material must fill the fixture cross section of the transmission line sensor with no air gaps at fixture walls. However, anisotropic materials can be measured in a transmission line waveguide.

Dielectric Spectroscopy techniques to estimate dielectric properties of biological subjects in vivo are discussed at, for example, U.S. Pat. Nos. 9,247,905, 7,315,767, 7,184,810, 8,200,307, 7,693,561. All of the solutions described therein are a variation of the coaxial probe method, and as a practical matter, even if unstated, all require the biological subject to be isotropic and homogeneous. These conditions virtually never occurs for biological in vivo subjects, so the techniques described above to estimate dielectric properties of biological subjects involve one or more mechanisms to attempt to correct for these variations.

For example, this first defect is magnified in in vivo subjects when attempting to perform dielectric spectroscopy though the skin into the body because these subjects are by definition anisotropic. A second defect occurs in all of the conventional approaches described above at the interface between the open-ended coaxial probe or probe-like structure and the surface of the skin. To date, despite tremendous effort, there is no generally acceptable electrical model of human skin. Various methods to correct for measurement defects arising from the skin-probe interface include blood profusion detectors and estimators, sweat detectors, temperature sensors, skin water content sensors and estimators, skin capacitance estimators, and air gap sensors and estimators. Theses sensors provide information the can generally indicate an electrical response variation in the skin that can be taken into account, but given that there are multiple variable, computing an accurate response becomes very complex. A third defect occurs in many of the solutions described above due to the fact that practical persistent data collection strategies to detect biological process anomalies, characterize nominal or steady state biological processes and identify novel biological processes to estimate the most probable state of the biological organism by observing it over time rather than ad hoc samples with great analytical precision is not possible due to in vivo subject's comfort.

Therefore, a need exists to overcome the problems with the prior art as discussed above.

SUMMARY OF THE INVENTION

The inventive apparatus eliminates this defect allowing the implementation of a persistent data collection strategy that emphasizes the ability of collection systems to linger, collecting data on demand, closely conforming to the natural unaltered shape of the living biological organism to which it is attached and thereby minimally interfering with normal life.

It is, therefore, an object of the invention to overcome the drawbacks of the prior art by providing an apparatus and method capable of generating, detecting and recognizing observed electromagnetic signals, which provides a beneficial persistent data collection strategy to detect biological process anomalies, determine nominal biological processes, characterize nominal biological processes, identify biological processes facilitating the formulation and execution of preemptive activities to deter or forestall anticipated adverse courses of action and provide remedial assessment and retreatment in near or real-time.

Embodiments of the inventive disclosure provide an apparatus and method capable of generating, detecting and recognizing biological processes in vivo though observed electromagnetic signal responses.

Embodiments of the inventive disclosure are directed towards dielectric spectroscopy measurement of in vivo biological organisms with anisotropic electrical and or mechanical properties where the inventive apparatus creates a virtual-image of a waveguide, i.e., waveguide element, that electrically is considered to be inside the biological organism while the actual physical waveguide is outside the biological organism.

For dielectric spectroscopy while it is known that the greatest electromagnetic signal is coupled into the specimen to generate the greatest possible E-field when the impedance is matched, it is of greater importance that the impedance is matched so the smallest E-field perturbations due to polarization differences between different analytes within the subject can be detected and measured.

The term "impedance matching" refers to making one impedance of a first signal medium, which could be electrical, mechanical, acoustic, optical, or dielectric, look like that of another medium through which the signal is propagated. Frequently, it becomes necessary to match a load impedance to the source or internal impedance of a driving source. The maximum power-transfer theorem says that to transfer the maximum amount of power from a source to a load, the load impedance should match the source impedance.

For dielectric spectroscopy in biological organisms the critical aspect is the extreme variability in capacitance between the signal emitter and the biological organism that is created by air gaps and for, in vivo human and animal subjects, additional problems of blood profusion, sweat, effects of temperature on the skin, water content of the skin and tissue, and most importantly, lack of a model of skin capacitance across frequency. Thus, a limiting factor in biological in vivo dielectric spectroscopy is anisotropy of the biological subject, in particular the skin of human and animal subjects.

Embodiments of the inventive disclosure circumvent this factor by using a plurality of dielectrics to create a wave guide structure with an impedance matching, as closely as possible, the electromagnetic impedance of the effective dielectric medium formed by the composite dielectric mixture of the anisotropic biological subject.

It will be understood by those skilled in the art that the inventive apparatus takes the general form of a transmission line embedded in anisotropic media where the effects of the strength of dielectric anisotropy follows these rules a) the E-field develops most strongly in the direction with highest permittivity; b) the degree to which E-field follows highest E is proportional to the strength of the anisotropy; c) impedance changes in the presence of the anisotropic medium, and d) the E-field actually "follows" the anisotropy.

The inventive apparatus, by reducing the anisotropy at the sensor to biological subject interface to near zero, causing this interface to become more isotropic by matching the dielectric properties of one to another, thereby causes the sensor to biological subject interface to disappear, effectively making the waveguide electrically image inside the biological organism while the actual physical waveguide sensor is outside the biological organism, thus allowing the anisotropy of the biological subject to dominate the measurement.

In the normal course of dielectric spectroscopy, the waveguide structure is then driven with electrical signal signals with a frequency content spread across an extremely wide frequency range from 100 kHz to 1 GHz.

The waveguide structure is coupled by a plurality of additional waveguide structures to a signal generator and receiver by means of appropriate connectors whereby the response of the biological organism to the input signals is recorded.

Therefore, the inventive apparatus overcomes the drawbacks of the prior art by providing an apparatus and method capable of generating, detecting and recognizing electromagnetic signal responses of components, which provides a beneficial persistent data collection strategy to detect biological process anomalies, determine nominal biological processes, characterize nominal biological processes, identify biological processes facilitating the formulation and execution of preemptive activities to deter or forestall anticipated adverse courses of action and provide remedial assessment and retreatment in near or real-time is thus achieved.

In accordance with the inventive disclosure, there is provided a microstrip waveguide structure for in vivo sensing of the electric permeability of an organism, wherein the electric permeability of the organism includes a known permeability component and an unknown permeability component, the microstrip waveguide structure includes a dielectric composite having a first side and a second side opposite the first side. The dielectric composite includes three dielectric regions organized linearly and including a first dielectric region, a second dielectric region, and a third dielectric region, wherein the second dielectric region, which is between the first and third dielectric regions, has an anisotropic electric permeability that is different than an electric permeability of the first dielectric region and the third dielectric region. The difference in permeability is in value and can also be in isotropy. The anisotropic electric permeability of the second dielectric region is selected to be substantially equal to the known permeability component of the electric permeability of the organism (e.g. within 20%). The microstrip waveguide further includes a microstrip transmission line formed on the first side of the dielectric composite, and has an input section formed on the first dielectric region, a radiator portion formed on the second dielectric region, and an output portion formed on the third dielectric region. There is also a ground plane formed on the second side of the dielectric composite.

In accordance with a further feature, the electric permeability of the first dielectric region is equivalent to the electric permeability of the third dielectric region.

In accordance with a further feature, the radiator portion of the microstrip transmission line is formed as a planar winding.

In accordance with a further feature, the planar winding is formed as an alternating meander.

In accordance with a further feature, the planar winding is formed as planar spiral.

In accordance with a further feature, the dielectric composite is curved.

In accordance with a further feature, the second dielectric region has a permittivity of 25-55.

In accordance with a further feature, the second dielectric region has a permittivity of 2-3.

In accordance with a further feature, the second dielectric region has a permittivity of 400 with a variation of +/−10%.

In accordance with a further feature, a thickness of the dielectric composite is less than half a height of the organism.

In accordance with a further feature, the electric permittivity of second dielectric region is selected to be substantially equal to the known permeability component of the electric permeability of the organism in a frequency range of 100 KHz to 220 MHz.

In accordance with a further feature, at least one of the first and third dielectric regions have an anisotropic permittivity.

In accordance with the inventive disclosure, there is provided a dielectric spectroscopy system for in vivo measurement of constituents of an organism, the organism having a first set of constituents having a first electric permittivity, and a second set of constituents having an electrical permittivity to be measured, the system includes a sensor having a dielectric composite having a first side and a second side opposite the first side. The dielectric composite comprising three dielectric regions organized linearly and including a first dielectric region, a second dielectric region, and a third dielectric region. The second dielectric region has an anisotropic electric permeability that is different than an electric permeability of the first dielectric region and the third dielectric region. The anisotropic electric permeability of the second dielectric region is selected to be substantially equal to the known permeability component of the electric permeability of the organism. The sensor further includes a microstrip transmission line formed on the first side of the dielectric composite and has an input section formed on the first dielectric region, a radiator portion formed on the second dielectric region, and an output portion formed on the third dielectric region. The sensor also has a ground plane formed on the second side of the dielectric composite. The system further includes a signal generator coupled to the input section configured to provide signals at a plurality of different frequencies, a coupler coupled to the input section for detecting reflected signals from the sensor, and a receiver coupled to the output section of the sensor to receive a transmitted signal.

In accordance with a further feature, the electric permeability of the first dielectric region is equivalent to the electric permeability of the third dielectric region.

In accordance with a further feature, the radiator portion of the microstrip transmission line is formed as a planar winding.

In accordance with the inventive disclosure, there is also provided a dielectric spectroscopy sensor for in vivo sensing of a living subject that includes a dielectric composite having a first side and a second side opposite the first side. The dielectric composite includes three dielectric regions organized in series and including a first dielectric region, a second dielectric region, and a third dielectric region. The second dielectric region is between the first and third dielectric regions and has an anisotropic electric permeability that is different than an electric permeability of the first dielectric region and the third dielectric region. The sensor further includes a microstrip transmission line formed on the first side of the dielectric composite and has an input section formed on the first dielectric region, a radiator portion formed on the second dielectric region, and an output portion formed on the third dielectric region. There is also a ground plane formed on the second side of the dielectric composite. The anisotropic electric permeability of the second dielectric region is selected so that, in a given frequency range the radiator portion appears to be electrically embedded in the organism.

In accordance with a further feature, the electric permeability of the first dielectric region is equivalent to the electric permeability of the third dielectric region.

In accordance with a further feature, wherein the radiator portion of the microstrip transmission line is formed as a planar winding.

In accordance with a further feature, wherein the planar winding is formed as an alternating meander.

In accordance with a further feature, wherein the planar winding is formed as planar spiral.

Although the invention is illustrated and described herein as embodied in an apparatus for in vivo spectroscopy, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the transmission line element unless otherwise indicated. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
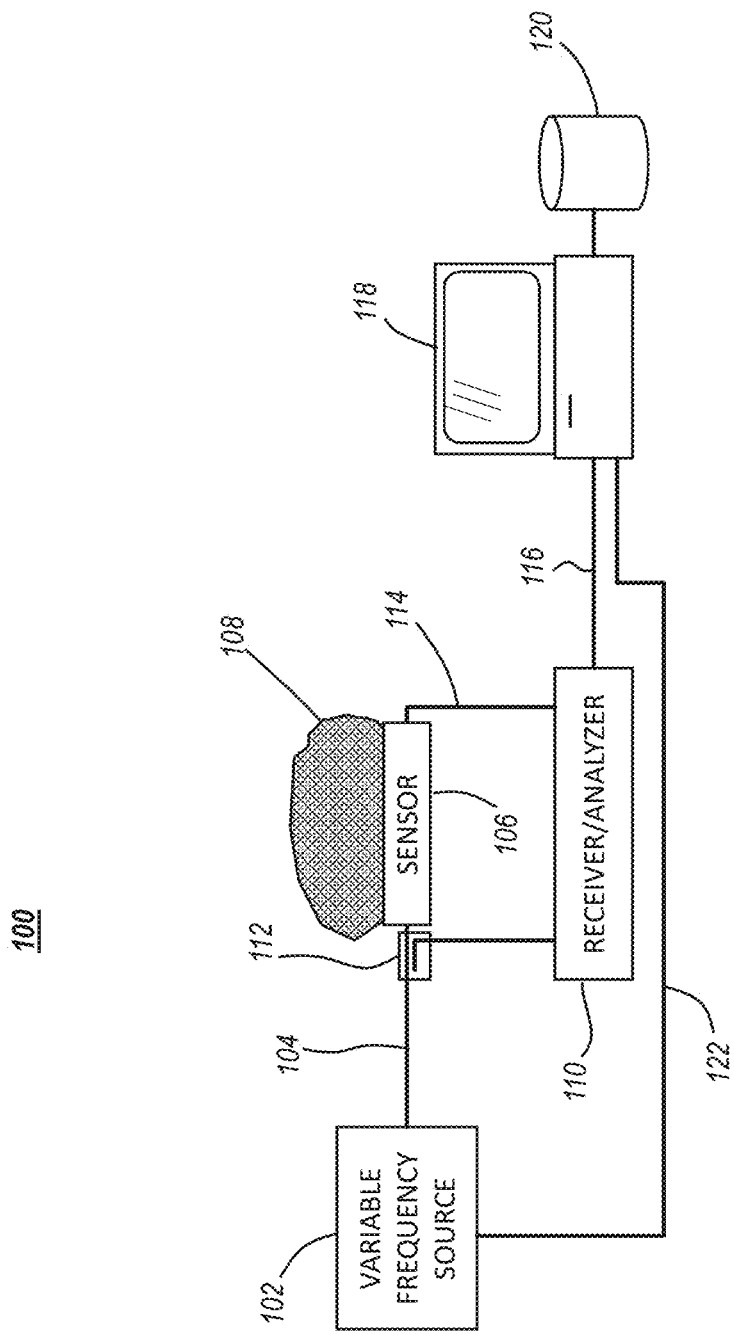
FIG. 1 is a block diagram of a dielectric spectroscopy system using a sensor having a composite dielectric construction, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

FIG. 1 is a block diagram of an in vivo dielectric spectroscopy system 100 using a sensor 106 having a composite dielectric construction, in accordance with some embodiments. The sensor is used to perform dielectric spectroscopy on a biological subject 108, which as shown here is a portion of a larger organism or other biological entity. Where the sensor 106 and the subject 108 meet there is an interface. For example, when the subject is an animal (or human), the sensor will be in contact with the subject's skin, which presents a variable and anisotropic dielectric component. Ordinarily the specific dielectric response of the skin, given temperature, blood profusion, sweat, etc. would have to be known specifically for using a conventional open-ended coaxial probe for dielectric spectroscopy. However, the sensor 106 is designed with anisotropic dielectric material that matches that of skin generally. As a result, the radiator portion of the sensor electrically images as being inside the subject, removing the effect of the sensor to skin interface. The sensor can be configured for particular subjects, such as, for example, humans, various animals, and various vegetative subjects such as avocados, bananas, and so on. Once the principle of the inventive disclosure is understood, those skilled in the art will be able to adapt the teachings herein to various test subjects.

A variable frequency generator 102 can be used to provide test signals at various frequencies. The test signals can be tone signals at regular frequency intervals or intervals of interest for a given test subject. The test signals are provided via a signal line 104 to the sensor 106. A receiver/analyzer 110 can then measure the signal output (e.g. $S_{21}$ parameter) of the sensor, as well as the reflected signal component (e.g. $S_{11}$ parameter). The reflected signal component can be measured using a coupler 112, while an output line 114 can be used to measure the transmitted signal component that passes through the sensor 106. The measured signal response parameters can be provided over a data line 116 or equivalent connection to a computer 118. The computer 118 can execute a software program that allows control of the variable frequency source 102, such as over control line 122. The computer can also analyze the results provided by the receiver/analyzer 110 by, for example, comparing the measurements at various frequencies with measurements produced with calibrated test samples that can be provided in a data store 120 that is either part of the computer 118, attached to the computer 118, or otherwise accessible by the computer 118 (e.g. over a network). The data store 120 can contain dielectric spectral response models for various components of interest which can be applied to measurement test results.

Figure 2:
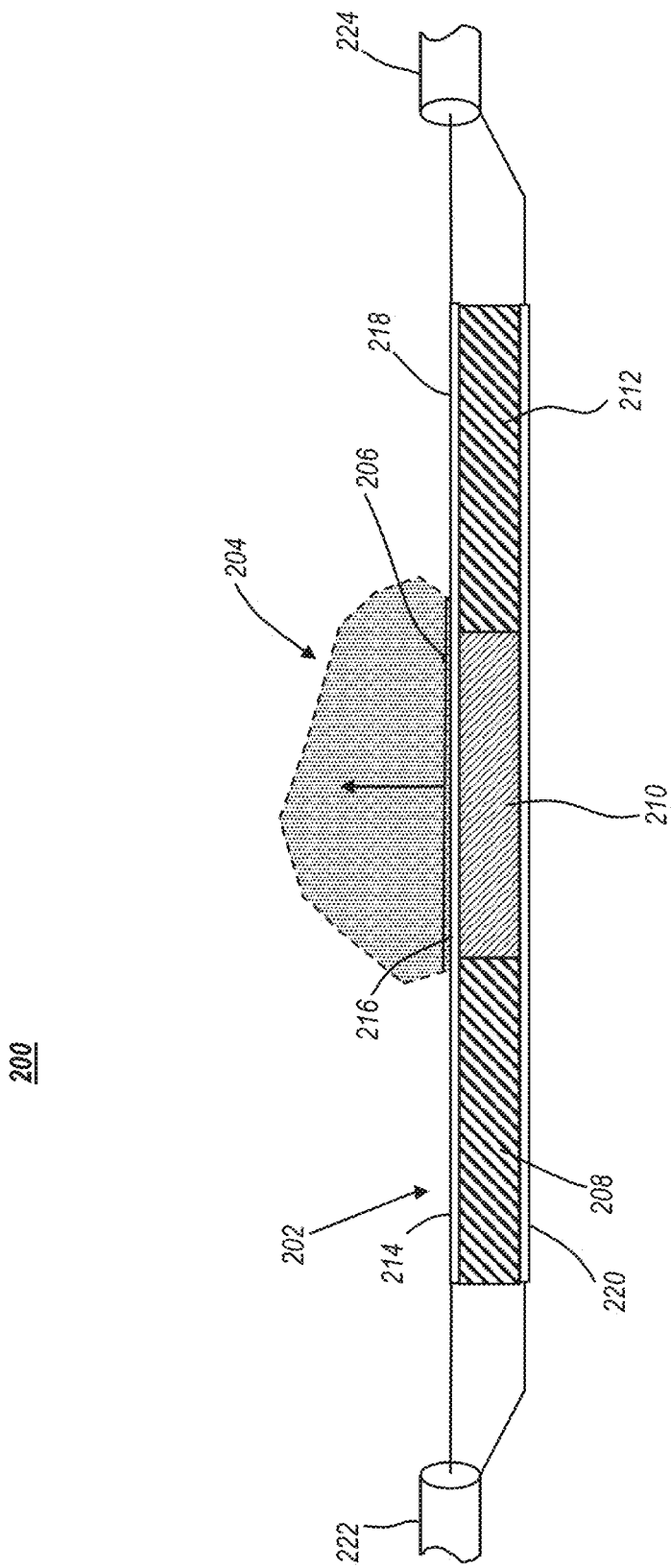
FIG. 2 is a side cross sectional view of a dielectric spectroscopy sensor designed in accordance with some embodiments, being used to measure the frequency response of a subject.
Figure 8:
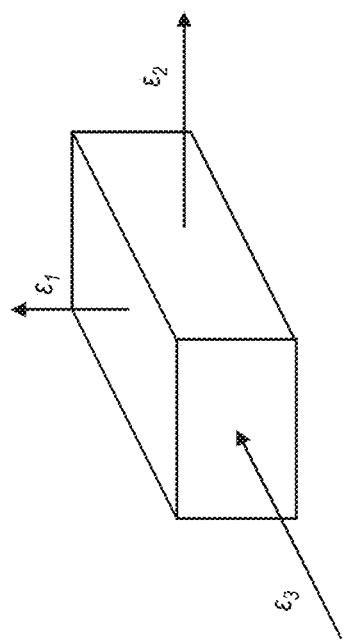
FIG. 8 shows an example of a material portion having anisotropic permittivity for use in a sensor for dielectric spectroscopy, in accordance with some embodiments.

FIG. 2 is a side cross sectional view of a dielectric spectroscopy sensor 200 designed in accordance with some embodiments, being used to measure the dielectric frequency response of a subject 204. The dielectric spectroscopy sensor 200 can be identical to sensor 106 of FIG. 1, and includes a dielectric composite structure 202 of three dielectric material regions arranged in a series, including a first dielectric region 208, a second dielectric region 210, and a third dielectric region 212. The second dielectric region 210 has a dielectric permittivity value that is different from that of the first and third dielectric regions 208, 212, respectively. By different it is meant that they have a different permittivity value across frequency, and can also exhibit a different isotrpy. In some embodiments the dielectric permittivity of the first and third dielectric regions 208, 212 can be equal. The second dielectric region 210 can further exhibit anisotropic permittivity, meaning the dielectric permittivity value depends on the direction in which the dielectric permittivity is measured. This is shown as an example in FIG. 8, where in three different dimensions, the dielectric material can have different permittivities ε1, ε2, ε3. On a subject-facing surface of the dielectric composite 202 is a microstrip transmission or waveguide formed by a conductive layer that includes an input section 214 at a first end of the dielectric composite 202 on the first dielectric region 208. The input section 214 is coupled to a radiator portion 216 on the second dielectric region 210. The radiator portion is designed to radiate electromagnetic waves outward, and into the subject 204. At the same time, electromagnetic waves will likewise radiate in the opposite direction, into the second dielectric region 210. The radiating portion 216 is coupled in series with an output section 218 on the third dielectric region 212. On the opposite, or bottom side of the dielectric composite 202 is a ground plane 220 that extends across all three dielectric regions 208, 210, 212. A feed line 222 can provide a signal from a frequency generator. A coupler can measure the reflected signal $S_{11}$ on the input line 222. A receive line 224 can receive the transmitted signal S21 that passes through the sensor 200, and provide the transmitted signal to a receiver/analyzer for measurement.

The subject 204 can include a skin 206 or similar external layer that separates the sensor 200 from the interior of the subject 204. This skin 206 represents a different dielectric permittivity from the interior of the subject 204, and which, with conventional dielectric spectroscopy techniques, must be known to a high degree in order to make measurements beyond the skin 206. However, using the dielectric composite, it is enough to approximate the permittivity of the skin 206. The electric permittivity of the second region, therefor, can be on the order of 25 to 55 for human subject. For dry trees it can be on the order of 2 to 3. For avocado fruits it can be on the order of about 400.

In the normal course of dielectric spectroscopy, the waveguide structure of the input section 214, radiating portion 216, and output section 218 is driven with electrical signal having a frequency content spread across an extremely wide frequency range, from 100 kHz to 1 GHz. The waveguide structure 214, 216, 218 is coupled by a plurality of additional waveguide structures 222, 224 to a signal generator and receiver by means of appropriate connectors whereby the response of the subject 204 to the input signals is measured and recorded. Each of the first, second, and third dielectric regions 208, 210, and 212 can be anisotropic in one, two or three dimensions, whereby each region 208, 210, 212 vary from each other in their complex electrical permittivity $e_r^*$ and complex magnetic permeability $\mu_r^*$ of dielectric regions 208, 210, 212 to match the subject 204 as closely as possible, meaning the skin 206 and other constituents that are not of interest. Thereby the constituents that are of interest have an unknown permittivity and permeability. The dimensions of the waveguide portions 214, 216, 218, as well as the dimensions of the dielectric regions 208, 210, 212 can be varied as desired to achieve a selected complex electrical permittivity $e_r^*$ and complex magnetic permeability $\mu_r^*$ as well as a desired overall impedance.

It may be appreciated by those skilled in the art that if the height of the subject 204 is much larger than the height of dielectric region 210 the effective complex electrical permittivity $e_r^*$ of the overall system will a mixture of the complex electrical permittivity of region 210 and the complex electrical permittivity of the subject 204. While a closed form expression may be possible, classical mixing rules such as the Maxwell Garnett formula and the Bruggeman formula do not function reliably, most probably because these rules require uniform inclusions in the composite matrix which is invalid for biological materials under test in vivo testing.

The value of the inventive impedance spectroscopy sensor 200 is in isolating individual phenomena responding to the electric signals in a multistep process. Assuming that each phenomena has a unique associated time constant, the various phenomena can be separated in the frequency domain. The phenomena of interest can include any of the various biological constituents of the subject 204. For example, blood sugar levels can be measured based on detecting and measuring the characteristic response of blood glucose. Although any kind of perturbation can be applied, most reported studies apply a small sinusoidal current perturbation to an equilibrium system and measure the corresponding voltage response. It will be further appreciated by those skilled in the art that the computation of the reflection and transmission values of the sensor 200 are not affected by the anisotropic nature of the biological materials under test. It has been found that the effective permittivity of the mixture of the human tissues in the wrist area falls between 30 and 55. Therefore, to measure constituents at the wrist area, the second dielectric region 210 should have a dielectric permittivity value in this region over the frequency range of interest, which will depend on which constituents are being measured/detected.

One of the most popular procedures for the complex electromagnetic permittivity characterization of materials as a function of frequency is the Nicolson Ross-Weir (NRW) method, (by extension the characterization of the complex beta-dispersion mechanism due to Maxwell-Wagner polarization), based on transmit/receive measurements of the specimen under test, in a transmission line, over frequency.

Figure 6:
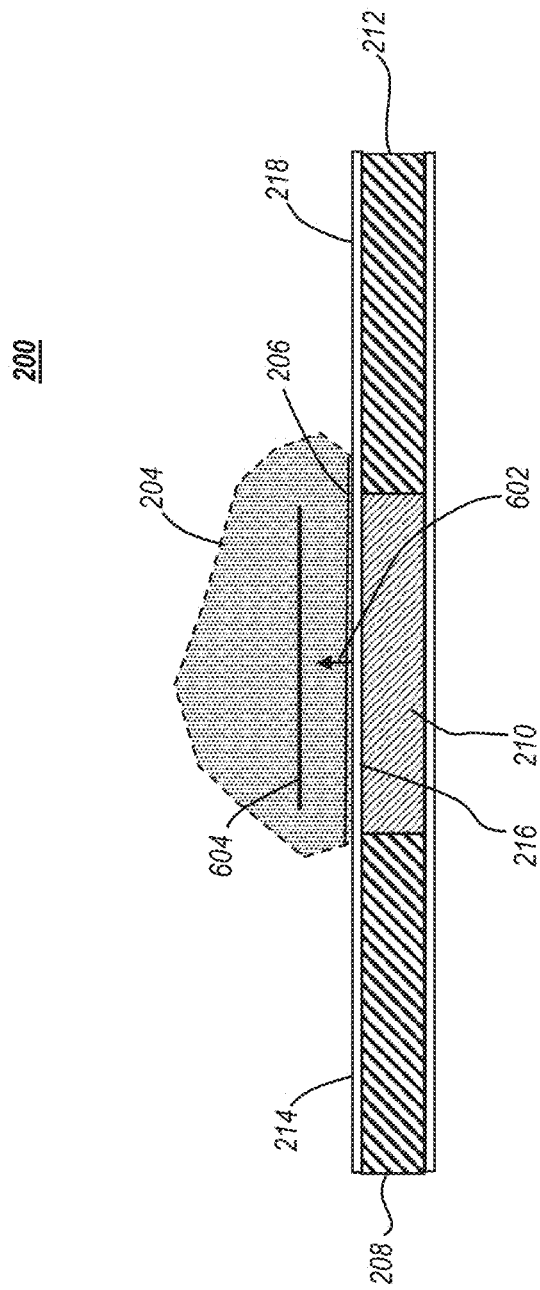
FIG. 6 is a side cross sectional view of a dielectric spectroscopy sensor indicating how the radiating portion images inside the subject, beyond the sensor to skin interface.

The properties of the materials under test are retrieved from their impedance and the wave velocities in the materials as a function of frequency. The main reason for the popularity of this method is that a closed form solution can be formed if the thickness of the specimen is less than an integer multiple of a half wavelength in the material, otherwise the method produces ambiguous results due to the $2\pi$ periodicity of the phase of the wave. In some embodiments the inventive sensor responses can be processed using a variation of the NRW technique in an alternative transmission line configuration based on technologies in common use such as the embedded RF microstrip to find an approximation of a dielectric effective medium that describes the macroscopic electrical properties of in vivo biological specimens as a composite material developed from averaging the multiple values of the constituents that make up the biological specimens (e.g. the subject 204) as a composite material. Thus, the inventive apparatus uses the behavior of electromagnetic fields under interface conditions, rather than boundary conditions, between two dielectric materials; a first one with completely known properties (e.g. region 210) and a second one with some combination of known and unknown properties (e.g. the subject 204), to measure the unknown properties of the second dielectric material (e.g. the subject 204). By approximating the dielectric response over frequency of some of the constituents of the subject 204 in dielectric region 210, those "known" constituents are removed from the effect as they are effectively matched by the second dielectric region 210. Thus, electrically, the radiating portion 216 effectively appears to be inside or embedded in the subject 204, as shown in FIG. 6. In FIG. 6 transverse or quasi-transverse waves 602 can be radiated into the subject 204. Because of the similarities of the permittivity of the dielectric region 210 and constituents of the subject 204 (such as the skin), the radiating portion 216 behaves effectively as if it were inside the subject 204 as indicated by line 604 as an embedded microstrip.

At the constituent level, the electromagnetic permittivity values of the live subject 204 vary and are inhomogeneous. Precise calculation of the many constituent values is nearly impossible. However, it is possible to produce acceptable approximations which in turn describe useful parameters and properties of the subject 204 as a whole. In this sense, effective medium approximations are descriptions of a medium (the subject 204) based on the properties and the relative fractions of its components which are derived from calculations. Thus, the inventive apparatus modifies the common RF embedded microstrip by using a sensor structure where the region 210 below the radiating portion 216 is filled with a dielectric with known properties, and the subject 204 above the radiating portion 216 has incompletely known properties. That is, some known and some unknown. Some of the dielectric properties over frequency of the subject 204 can be known a priori and the second dielectric region 210 under the radiating portion 216 can be been created with electrical characteristics similar to the known dielectric properties of the subject 204, and in combination with the ground plane 220 the radiation portion 216 acts as an embedded microstrip transmission line that is electrically buried in the subject 204 while remaining physically outside the subject 204.

The sensor 200 can be fed as a transmission line and transmit/reflected measurements of the effective medium formed by the combination of the subject 204 and known dielectric of the dielectric composite 202 can be made using the transmission line method considering all three parts of the sensor; the input section 214 on the first dielectric region 208, the radiating portion 216 on the second dielectric region 210, and the output section 218 on the third dielectric region 212.

Properties of the subject 204 under test are retrieved from their impedance and the wave velocities in the materials as a function of frequency. The electromagnetic permittivity characterization of the dielectric effective medium created by the known dielectric (208, 210, 212) subject 204 can be obtained by the Nicolson Ross-Weir (NRW) method, and by extension the characterization beta-dispersion mechanism due to Maxwell-Wagner polarization, whereby properties of the subject 204 under test are retrieved in vivo.

Another method for utilizing the inventive sensor 200 to determine complex electromagnetic permittivity as a function of frequency is the NIST iterative method which performs the calculation using a Newton-Raphson's root finding method, and is suitable for permittivity calculation only. It utilizes all four scattering parameters ($S_{11}$, $S_{21}$, $S_{12}$, $S_{22}$) or a pair ($S_{11}$, $S_{21}$) of scattering parameters of the subject 204 to calculate the reflection and transmission coefficient. This method works well if a good initial guess is available, and bypasses the inaccuracy peaks that exist in the NRW method when the sample thickness is an integer multiple of one-half wavelength $n\lambda g/2$. It is suitable for long samples and characterizing low loss materials.

Yet another method for the utilizing the inventive sensor 200 to determine complex electromagnetic permittivity of materials as a function of frequency is the non-iterative method, which is similar to the NRW method but with a different formulation, and it is suitable for permittivity calculation for the case where permeability $\mu_r=1$. It utilizes all four ($S_{11}$, $S_{21}$, $S_{12}$, $S_{22}$) scattering parameters or just two ($S_{11}$, $S_{21}$) scattering parameters of the subject 204 to calculate the reflection and transmission coefficients. This method has the advantage of being stable over a whole range of frequencies for an arbitrary sample length, and is based on a simplified version of NRW method. No divergence is observed at frequencies corresponding to multiples of one-half wavelength in the sample. It does not need an initial estimation of permittivity and can perform the calculation very fast. The accuracies of this method are comparable to the iterative method, and uses a partly different formulation from the NRW method. It can be easily extended to other measuring samples, for example micro-strip or coplanar lines. It also has the permittivity and permeability appear in the expression of the effective electromagnetic parameters. The effective electromagnetic parameters represent a propagation mode.

Yet another method for the utilizing the inventive sensor 200 to determine complex electromagnetic permittivity as a function of frequency is the short circuit line (SCL) method which is a one port measurement on waveguides. The SCL method performs the calculation using the same Newton-Raphson's numerical approach as in the NIST iterative method and is suitable for permittivity calculation only. It utilizes only the $S_{11}$ parameter of subject 204 to calculate the reflection coefficient. The method requires a good initial guess in order to obtain an accurate result. The method also requires the sample length and position to known for accurate measurements.

Figure 3:
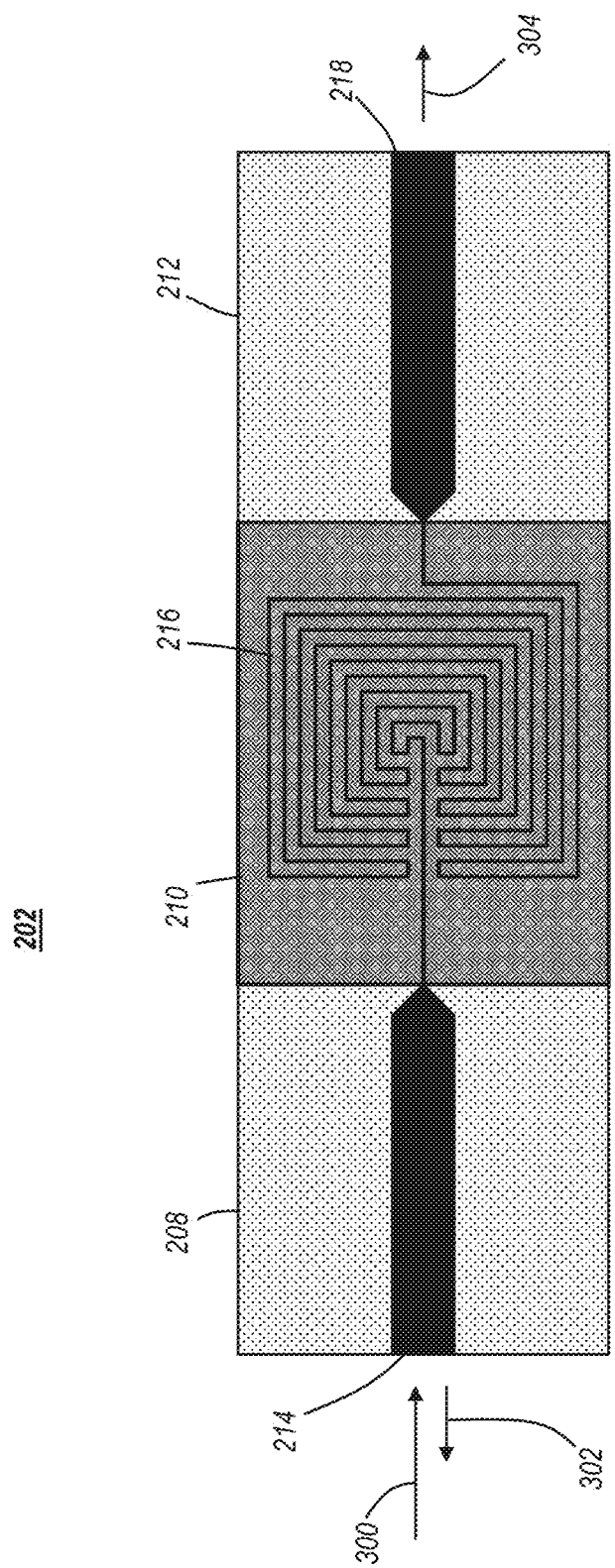
FIG. 3 is a top view of a dielectric spectroscopy sensor, in accordance with some embodiments.

FIG. 3 is a top view of a dielectric spectroscopy sensor 202, in accordance with some embodiments. The microstrip waveguide is comprised of an input section 214 on the first dielectric region 208, a radiation portion 216 on the second dielectric region 210, and the output section 218 on the third dielectric region 212. A signal can be applied to the structure as indicated by arrow 300, resulting in a reflected wave indicated by arrow 302 and a transmitted wave indicated by 304. The values of these responses can be used, using the above-described methods, to determine the "unknown" permittivity of constituents of a subject (e.g. 204) in contact with the radiation portion 216. As shown here, the radiating portion is a center-fed fully alternating meander, meaning the conductive trace starts at the center, traverses to one side, then travels back around itself to the other side, and so on, and then couples to the output section 218.

Figure 4:
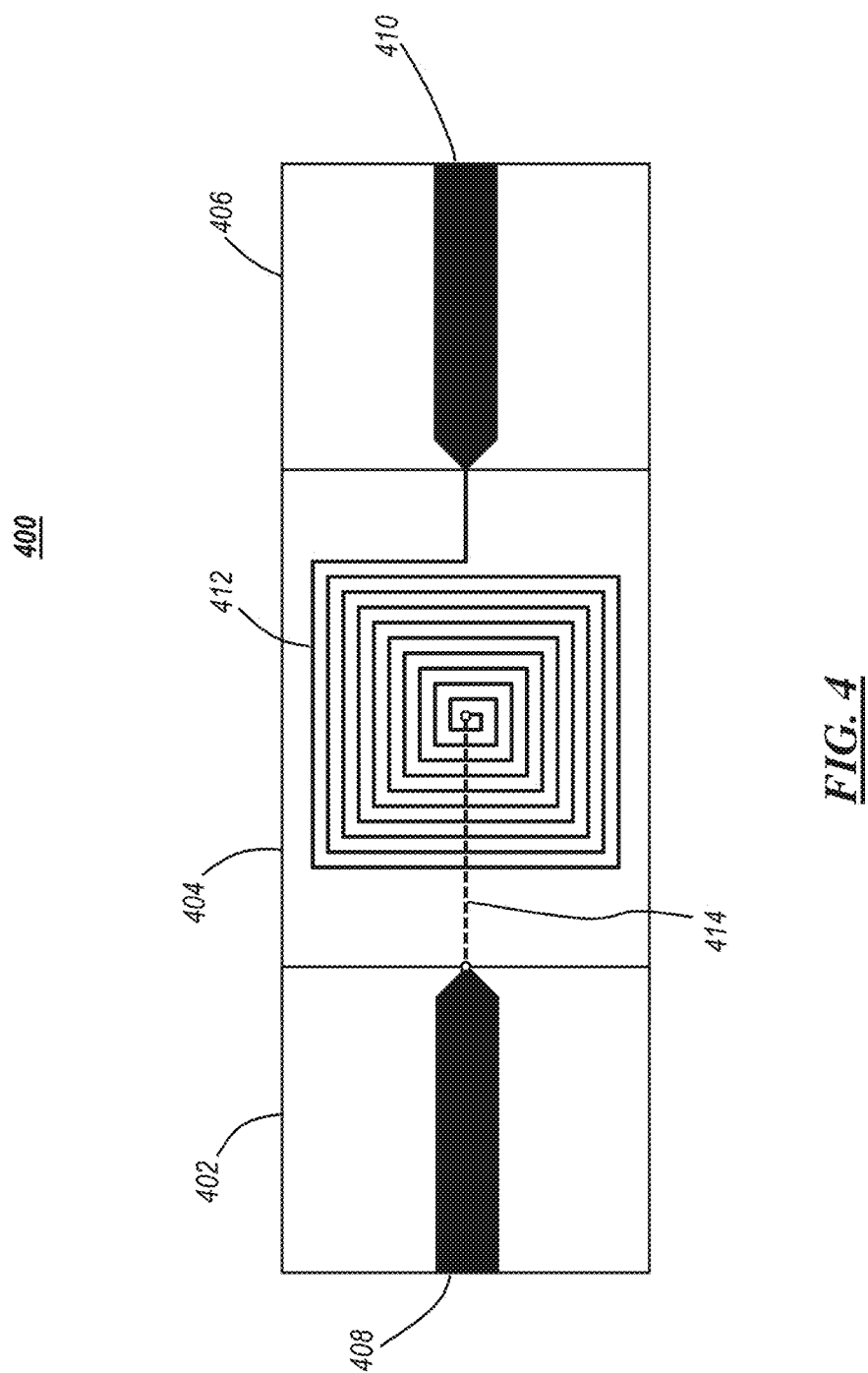
FIG. 4 is a top view of a dielectric spectroscopy sensor, in accordance with some embodiments.

FIG. 4 is a top view of a dielectric spectroscopy sensor 400, in accordance with some embodiments. The sensor 400 is substantially similar to the sensor 202, including a first dielectric portion or region 402, a second dielectric region 404, and a third dielectric region 406. The input section 408 of the microstrip waveguide structure is formed on the first dielectric region 402. A radiating portion or element 412 is formed on the second dielectric region 404 and is fed by the input section 408. The output section 410 is formed on the third dielectric region 406 and is coupled to an end of the radiation portion 412. As shown here, the radiation portion 412 is a center-fed planar spiral winding. A feed line 414 connects the input section 408 to the center of the radiation portion 412 and traverses the second dielectric portion 404 under the winding traces on the top of the second dielectric portion 404. The dielectric permittivity of the second dielectric region 404 is selected to be approximate to that of certain constituents of a given test subject in order to measure the permittivity of the other constituents of the subject.

Figure 5:
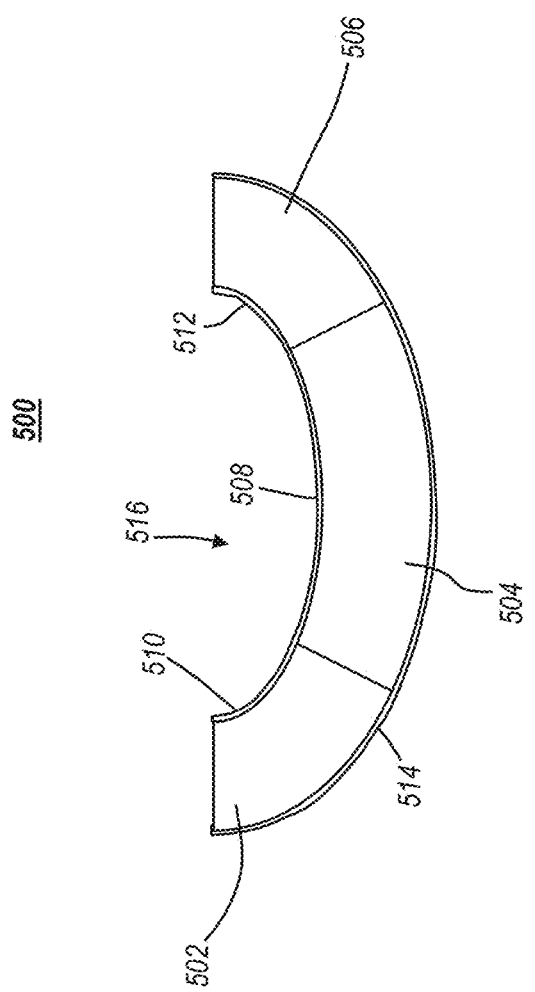
FIG. 5 is a side view of a curved dielectric spectroscopy sensor, in accordance with some embodiments.

FIG. 5 is a side view of a curved dielectric spectroscopy sensor 500, in accordance with some embodiments. The sensor 500 can be curved or otherwise shaped to receive a correspondingly-shaped subject. For example, the curved sensor 500 forms a recess 516 in which the wrist of a patient can be received and placed in contact with the sensor 500. The sensor 500 comprises three dielectric regions 502, 504, and 506. The permittivity of dielectric region 504 is selected to substantially match constituents of the subject not being tested in the frequency ranges used for the constituents being tested or determined, and is different than the permittivity of dielectric regions 502, 506. Thus a microstrip waveguide is comprised of an input section 510 on the first dielectric region 502, the input section 510 feeds a radiating portion 508 on the second dielectric region 504, and the output of the radiation portion 508 is coupled to an output section 512 on the third dielectric region 506. A ground plane 514 is on the opposite side of the dielectric regions 502, 504, 506 from the microstrip waveguide elements 510, 508, 512.

Figure 7:
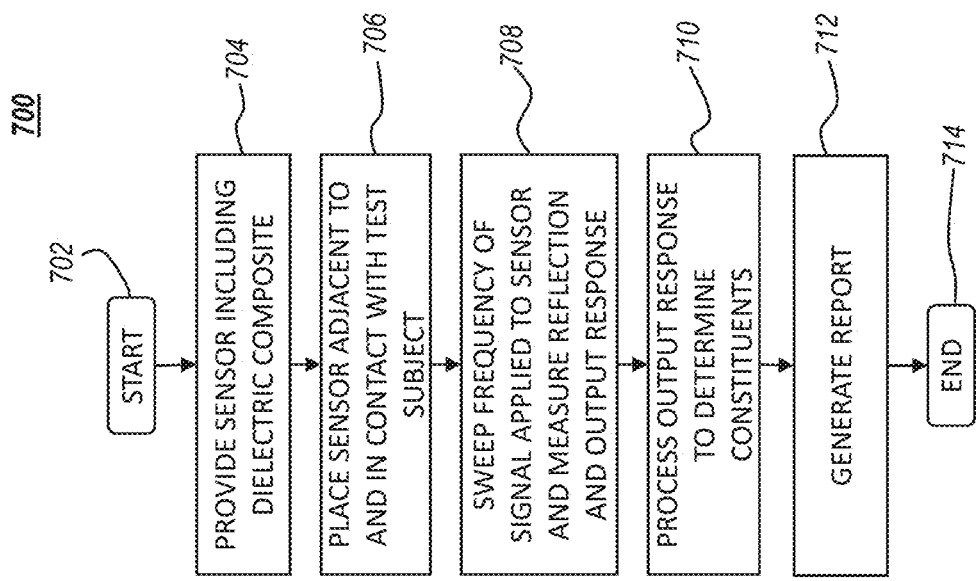
FIG. 7 is a flow chart diagram of a method for using a dielectric spectroscopy sensor, in accordance with some embodiments.

FIG. 7 is a flow chart diagram of a method 700 for using a dielectric spectroscopy sensor, in accordance with some embodiments. At the start 702 a subject for testing has been identified, either specifically or generally. In step 704 a sensor and system such as that of FIG. 1 is provided where the sensor includes a dielectric composite formed of three sections arranged in a series with a microstrip waveguide structure placed on one side of the dielectric composite, and a ground plane on an opposite side. The microstrip waveguide structure comprised an input section on the first dielectric region, a radiating element on the second dielectric region, and an output section on the third dielectric region. The permittivity of the second dielectric section is selected to be equal to that of certain constituents of the subject being tested that are known. These electrical properties will vary based on the subject and the constituents being measured. Further, the permittivity of the first and third dielectric regions are different than that of the second dielectric region.

in step 706 the sensor is placed in contact with the subject, and specifically the radiation element of the microstrip waveguide is placed facing the subject. In step 708 a series of signals at various frequencies is applied to the sensor, and for each frequency used, the reflected and transmitted signals are measured. The reflected signal is measured at the input, and the transmitted signal is measured at the output of the sensor (e.g. on the other side of the radiating element). In step 710 the measured reflected and transmitted signals are processed and compared to known model responses of constituents being tested. In step 712 a report can be prepared or generated, and then the method is done 714.

In practice, using a sensor configured as shown and described herein, a transverse electromagnetic (TEM) wave is launched from the radiation element as a quasi TEM wave and transformed by elements microstrip waveguide in combination with the resulting impedance produced by the dielectric composite and subject being tested. E-fields are developed in subject by the combination of the second dielectric region and the radiation element and ground plane. Since the subject and the second dielectric region are identical, or nearly so, the anisotropy introduced by the waveguide structure at the interface between the subject and the radiating element is reduced to near zero, causing this interface to become more isotropic by matching the dielectric properties of one to another. Thus, the interface effectively disappears, making the radiating element electrically image inside the subject while the actual physical sensor is outside the subject.

The TEM wave passing through the radiating element is transformed by the output section and ground plane in combination with the third dielectric element to the nominal impedance of a receiver. It will be appreciated by those skilled in the art that the impedance of the microstrip waveguide configuration described above need not have a nominal impedance of 50 ohms. It will be further appreciated by those skilled in the art that the dielectric regions can be anisotropic in one, two or three dimensions, and that the complex electrical permittivity and complex magnetic permeability of the dielectric composite regions are selected to match the biological specimen as closely as possible.

It will also be appreciated by those skilled in the art that the dimensions of each element can vary to achieve the desired permittivity and permeability by adjusting or changing the width and thickness of the microstrip waveguide elements to determine the desired overall impedance. It will be further appreciated that the resulting permittivity and permeability of the sensor in combination with the subject can be measured using various methods as described herein.

Accordingly, a sensor forming a microstrip waveguide structure, and various associated methods have been disclosed that allow a radiator portion of the microstrip waveguide to image effectively inside of a subject being tested to that the permittivity of certain constituents of the subject can be measured. The inventive arrangement eliminates the need for invasive techniques and allows for in vivo testing of the subject. Accordingly, dynamic processes in the subject can be monitored on an ongoing basis without disrupting the subject or causing discomfort in the case of animal/human subjects.

What is claimed is:
1. A microstrip waveguide structure for in vivo sensing of an electric permeability of an organism, wherein the electric permeability of the organism includes a known permeability component and an unknown permeability component, the microstrip waveguide structure comprising:

a dielectric composite having a first side and a second side opposite the first side, the dielectric composite comprising three dielectric regions organized linearly and including a first dielectric region, a second dielectric region, and a third dielectric region, wherein the second dielectric region has an anisotropic electric permeability that is different than an electric permeability of the first dielectric region and the third dielectric region, and wherein the anisotropic electric permeability of the second dielectric region is selected to be substantially equal to the known permeability component of the electric permeability of the organism;

a microstrip transmission line formed on the first side of the dielectric composite and having an input section formed on the first dielectric region, a radiator portion formed on the second dielectric region, and an output portion formed on the third dielectric region; and a ground plane formed on the second side of the dielectric composite.

2. The microstrip waveguide structure of claim 1, wherein the electric permeability of the first dielectric region is equivalent to the electric permeability of the third dielectric region.

3. The microstrip waveguide of claim 1, wherein the radiator portion of the microstrip transmission line is formed as a planar winding.

4. The microstrip waveguide of claim 3, wherein the planar winding is formed as an alternating meander.

5. The microstrip waveguide of claim 3, wherein the planar winding is formed as planar spiral.

6. The microstrip waveguide of claim 1, wherein the dielectric composite is curved.

7. The microstrip waveguide of claim 1, wherein the second dielectric region has a permittivity of 25-55.

8. The microstrip waveguide of claim 1, wherein the second dielectric region has a permittivity of 2-3.

9. The microstrip waveguide of claim 1, wherein the second dielectric region has a permittivity of 400 with a variation of +/−10%.

10. The microstrip waveguide of claim 1, wherein a thickness of the dielectric composite is less than half a height of the organism.

11. The microstrip waveguide of claim 1, wherein the electric permittivity of second dielectric region is selected to be substantially equal to the known permeability component of the electric permeability of the organism in a frequency range of 100 KHz to 220 MHz.

12. The microstrip waveguide of claim 1, wherein at least one of the first and third dielectric regions have an anisotropic permittivity.

13. A dielectric spectroscopy system for in vivo measurement of constituents of an organism, the organism having a first set of constituents having a first electric permittivity, and a second set of constituents having an electrical permittivity to be measured, the system comprising:

a sensor having:
a dielectric composite having a first side and a second side opposite the first side, the dielectric composite comprising three dielectric regions organized linearly and including a first dielectric region, a second dielectric region, and a third dielectric region, wherein the second dielectric region has an anisotropic electric permeability that is different than an electric permeability of the first dielectric region and the third dielectric region, and wherein the anisotropic electric permeability of the second dielectric region is selected to be substantially equal to a known permeability component of an electric permeability of the organism;

a microstrip transmission line formed on the first side of the dielectric composite and having an input section formed on the first dielectric region, a radiator portion formed on the second dielectric region, and an output portion formed on the third dielectric region; and a ground plane formed on the second side of the dielectric composite;

a signal generator coupled to the input section configured to provide signals at a plurality of different frequencies;

a coupler coupled to the input section for detecting reflected signals from the sensor; and a receiver coupled to the output section of the sensor to receive a transmitted signal.

14. The dielectric spectroscopy system of claim 13, wherein the electric permeability of the first dielectric region is equivalent to the electric permeability of the third dielectric region.

15. The dielectric spectroscopy system of claim 13, wherein the radiator portion of the microstrip transmission line is formed as a planar winding.

16. A dielectric spectroscopy sensor for in vivo sensing of a living subject, comprising:

a dielectric composite having a first side and a second side opposite the first side, the dielectric composite comprising three dielectric regions organized in series and including a first dielectric region, a second dielectric region, and a third dielectric region, wherein the second dielectric region is between the first and third dielectric regions and has an anisotropic electric permeability that is different than an electric permeability of the first dielectric region and the third dielectric region;

a microstrip transmission line formed on the first side of the dielectric composite and having an input section formed on the first dielectric region, a radiator portion formed on the second dielectric region, and an output portion formed on the third dielectric region; and a ground plane formed on the second side of the dielectric composite;

wherein the anisotropic electric permeability of the second dielectric region is selected so that, in a given frequency range the radiator portion appears to be electrically embedded in the organism.

17. The dielectric spectroscopy sensor of claim 16, wherein the electric permeability of the first dielectric region is equivalent to the electric permeability of the third dielectric region.

18. The dielectric spectroscopy sensor of claim 16, wherein the radiator portion of the microstrip transmission line is formed as a planar winding.

19. The dielectric spectroscopy sensor of claim 18, wherein the planar winding is formed as an alternating meander.

20. The dielectric spectroscopy sensor of claim 18, wherein the planar winding is formed as planar spiral.

* * * * *